US006583129B1

(12) United States Patent
Mazer et al.

(10) Patent No.: US 6,583,129 B1
(45) Date of Patent: Jun. 24, 2003

(54) ADMINISTRATION OF NON-ORAL ANDROGENIC STEROIDS TO WOMEN

(75) Inventors: Norman A. Mazer, Salt Lake City, UT (US); Theresa Rosario-Jansen, Loveland, OH (US)

(73) Assignee: Watson Pharmaceuticals, Inc., Corona, CA (US)

( * ) Notice: Subject to any disclaimer, the term of this patent is extended or adjusted under 35 U.S.C. 154(b) by 0 days.

(21) Appl. No.: 09/591,141

(22) Filed: Jun. 9, 2000

Related U.S. Application Data

(60) Provisional application No. 60/138,851, filed on Jun. 11, 1999, provisional application No. 60/138,854, filed on Jun. 11, 1999, and provisional application No. 60/139,323, filed on Jun. 11, 1999.

(51) Int. Cl.[7] .......................... A61K 31/59; A61K 31/56; A61K 31/58
(52) U.S. Cl. .................. 514/167; 514/169; 514/170; 514/172; 514/177; 514/178; 514/182
(58) Field of Search .......................... 424/400; 514/167, 514/169, 170, 172, 177, 178, 182

(56) References Cited

U.S. PATENT DOCUMENTS

| | | |
|---|---|---|
| 4,849,224 A | 7/1989 | Chang et al. |
| 4,983,395 A | 1/1991 | Chang et al. |
| 5,122,383 A | 6/1992 | Heiber et al. |
| 5,152,997 A | 10/1992 | Ebert et al. |
| 5,460,820 A | 10/1995 | Ebert et al. |
| 5,550,107 A | 8/1996 | Labrie |
| 5,855,920 A | 1/1999 | Chein |
| 5,962,021 A | 10/1999 | Hughes, Jr. et al. |

FOREIGN PATENT DOCUMENTS

GB 2167662 * 6/1986

OTHER PUBLICATIONS

Sarrel et al, Estrogen and estrogen–androgen replacement in postmenopausal women dissatisfied with estrogen–only therapy, 1998, J. Reprod. Med. vol. 43(10), pp. 847–856.*

Dunn, et al., Transport of Steroid Hormones: Binding of 21 Endogenous Steroids to Both Testosterone–Binding Globulin and Corticosteroid–Binding Globulin in Human Plasma *Journal of Clinical Endocrinology and Metabolism,* vol.53:58–67 (1981).

Rosner et al., Sex Hormone–Binding Globulin Mediates Steroid Hormone Signal Transduction at the Plasma Membrane, *J. Steroid Biochem. Mol. Biol.* vol. 69:481–5 (1999).

Petra, P.H. The plasma Sex Steroid Binding Protein (SBP or SHBG). A Critical Review of Recent Developments on the Structure Molecular Biology, and Function, *J. Steroid Biochem. Mol. Biol.*, vol. 40:735–53 (1991).

Khan et al., Radioimmunoassay for Human Testosterone–Estradiol–Binding Globulin, *J. Clinical Endocrinology and Metabolism*, vol. 54:705–710 (1982).

Bond et al., Sex Hormone Binding Globulin in Clinical Perspective, *Acta. Obstet. Gynecol. Scand.*, vol. 66:255–262 (1987).

(List continued on next page.)

*Primary Examiner*—Alton N Pryor
(74) *Attorney, Agent, or Firm*—Thorpe North & Western, LLP

(57) ABSTRACT

The present invention provides compositions, methods, and kits for improving health in a woman having elevated SHBG levels, or who is receiving oral estrogen supplementation, by non-orally administering an effective amount of an androgenic steroid. Further, the present invention provides compositions, methods, and kits for coadministering an effective amount of an orally administered estrogen and an effective amount of a non-orally administered androgenic steroid for women in need of estrogen supplementation.

30 Claims, 1 Drawing Sheet

OTHER PUBLICATIONS

Miller, et al. Transdermal Testosterone Administration in Women with Acquired Immunodeficiency Syndrome Wasting: A Pilot Study, *J. of Clinical Endocrinology and Metabolism*, vol. 83: 2717–2725 (1998).

Furuyama et al., Radioimmunoassay for Plasma Testosterone, *Steroids*. 1970;16:415–428.

Vermeulen et al., A Critical Evaluation of Simple Methods for the Estimation of Free Testosterone in Serum, *J. of Clinical Endocrinology and Metabolism* vol. 84:3666–3672 (1999).

Nankin et al. Daytime Titers of Testosterone, LH, Estrone, Estradiol, and Testosterone–Binding Protein: Acute Effects of LH and LH–Releasing Hormone in Men, *J. Clinical Endocrinology Metabolism*, vol. 41:271–81 (1975.

Winters et al. The Analog Free Testosterone Assay: Are the Results in Men Clinically Useful?, *Clinical Chemistry* vol. 44:2178–2182 (1998); see also, Vermuelen et al. (1999).

Mathor et al., Free Plasma Testosterone Levels During the Normal Menstrual Cycle, *J. Endocrinol Invest* vol. 8:437–41 (1985).

Derogatis Interview for Sexual Functioning, Derogatis, L., The Derogatis iInterview for Sexual Functioning (DISF/DISF–SR): an introductory report, *J. Sex. Marital Ther.* Winter 23(4):291–304 (1997).

Derogatis et al., Psychological assessment measures of human sexual functioning in clinical Trials, *Int. J. Impot. Res.*, May 10 Suppl. 2:S13–20 (1998).

Beck Depression Inventory (Beck et al 1961).

Psychological General Well–being Index (Dupuy 1984).

Mathers et al. Menopause and Tear Function: The Influence of Prolactin and Sex Hormones on Human Tear Production, *Cornea* vol. 17:353–8 (1998).

Vermuelen et al. Metabolic Clearance Rate and Interconversion of Androgens and the Influence of the Free Androgen Fraction, *J. Clinical Endocrinology and Metabolism* vol. 48:320–326 (1979).

Longcope et al. Free Estradiol. Free Testosterone, and Sex Hormone–Binding Globulin in Perimenopausal Women, *J. Clinical Endocrinology and Metabolism* vol. 64:513–518 (1987).

* cited by examiner

ADMINISTRATION OF NON-ORAL ANDROGENIC STEROIDS TO WOMEN

RELATED APPLICATIONS

This application claims priority to United States Provisional Patent Applications Serial No: 60/138,851; Serial No: 60/138,854, and Serial No: 60/139,323, each of which was filed on Jun. 11, 1999. Each of these applications is hereby incorporated by reference.

THE FIELD OF THE INVENTION

This invention broadly relates to the administration of androgens to women. Accordingly, this invention covers the fields of pharmaceutical sciences and medicine.

BACKGROUND OF THE INVENTION

It is known that a functional level of androgenic hormones in females promotes sexual health and activity, feelings of well being, maximizes muscle mass and function, and inhibits bone loss. Further, a functional level of androgenic hormones may promote cardiovascular and coronary health, decrease breast tenderness, decrease vasomotor instability, modulate immune function, enhance certain cognitive abilities, improve urogential health, reduce estrogen supplementation related side effects, and provide direct neuroprotective effects.

The attainment of functional levels of androgenic hormones in women, such as testosterone, may be influenced by the serum concentrations of sex hormone binding globulin (SHBG). SHBG is a protein produced by the liver that binds sex hormones such as testosterone and estradiol in the blood. The SHBG-bound sex hormones are generally "non-functional", i.e., unavailable to exert biological action at sex hormone receptors in target tissues and/or undergo clearance from the blood.

Use of oral estrogens raises serum levels of SHBG. SHBG levels are also elevated in various conditions, e.g., hyperthyroidism and pregnancy, and by certain other medications, e.g., anti-convulsants. Elevated SHBG levels alter the levels of androgenic hormones and the doses needed to achieve functional levels.

The present invention provides methods, compositions, and kits to achieve functional levels of androgenic steroids in women with elevated SHBG levels and thus improve their health.

SUMMARY OF THE INVENTION

Accordingly, the present invention provides a method and kit for improving health in a woman who has an elevated or substantially elevated level of sex hormone binding globulin (SHBG). Additionally, the present invention provides a method and kit for improving health in a woman receiving oral estrogen supplementation. Further, the present invention provides a method and kit for improving health in a woman in need of oral estrogen supplementation.

In one aspect, such methods include non-orally administering an androgenic steroid, in an amount sufficient to provide a therapeutic effect in the presence of elevated, or substantially elevated SHBG levels. In another aspect, such methods include non-orally administering an androgenic steroid, in an amount sufficient to provide a therapeutic effect in the presence of an oral estrogen administration. In yet another aspect, such methods include co-administering an effective amount of an orally administered estrogen and an amount of a non-orally administered androgenic steroid which is sufficient to provide a therapeutic effect in the presence of oral estrogen administration.

Examples of specific androgenic steroids which may be utilized include but are not limited to: testosterone, methyltestosterone, androstenedione, adrenosterone, dehydroepiandrosterone, oxymetholone, fluoxymesterone, methandrostenolone, testolactone, pregnenolone, 17α-methylnortestosterone, norethandrolone, dihydrotestosterone, danazol, oxymetholone, androsterone, nandrolone, stanozolol, ethylestrenol, oxandrolone, bolasterone and mesterolone, testosterone propionate, testosterone cypionate, testosterone phenylacetate, and testosterone enanthate, testosterone acetate, testosterone buciclate, testosterone heptanoate, testosterone decanoate, testosterone caprate, testosterone isocaprate, isomers and derivatives thereof, and a combination thereof.

The amount of androgenic steroid to be administered may be measured according to several different parameters. In one aspect, the amount of androgenic steroid administered may be an amount sufficient to achieve a therapeutic effect equivalent to a total testosterone serum level of from about 15 to about 1000 ng/dl. In another aspect of the present invention, the amount of androgenic steroid administered may be an amount sufficient to achieve a therapeutic effect equivalent to a free testosterone serum level of from about 0.5 to about 30 pg/ml. In a further aspect of the present invention, the amount of androgenic steroid administered may be an amount sufficient to achieve a therapeutic effect equivalent to a bioavailable testosterone serum level of from about 1 to about 70 ng/dl. In yet another aspect of the present invention, the amount of androgenic steroid administered may be an amount sufficient to achieve a therapeutic effect equivalent to a testosterone dosage of at least about 50 mcg/day.

Examples of specific estrogens which may be utilized in connection with the method of the present invention include but are not limited to: 17β-estradiol, 17α-estradiol, conjugated equine estrogen, esterified estrogen, micronized estradiol, sodium estrogen sulfate, ethinyl estradiol, estrone, tibolone, selective estrogen receptor modulators (SERM's), phytoestrogens, isomers and derivatives thereof, and a combination thereof. In one aspect of the invention, the amount of estrogen administered may be a dosage sufficient to achieve a therapeutic effect equivalent to a conjugated equine estrogen dosage of about 0.2 to about 3.0 mg/day.

Various forms of non-oral administration of androgen may be employed in accordance with the methods of the present invention, including but not limited to: topical administration, or parenteral administration, or a combination thereof. In one aspect, the forms of topical administration include without limitation, transdermal, or transmucosal, or sublingual, or a combination thereof. In another aspect, the parentarel forms of administration include without limitation, intramuscular injection, or subcutaneous implantation, or a combination thereof.

A progestin may be coadministered with the androgenic steroid and the estrogen, when desired. In one aspect, the progestin administration may be an amount sufficient to provide endometrial safety during oral estrogen administration. In another aspect, the progestin administration may be an amount sufficient to provide effective contraception.

There are many indicators of the improved health which may occur as a result of the method of the present invention. Of particular note, without limitation thereto, are the restoration, enhancement, improvement, or prevention of characteristics such as: sexual desire, frequency of sexual activity, stimulation to sexual organs, ability to achieve orgasm, pleasure in sexual activity, vital energy, sense of well-being, mood and sense of emotional well being, shyness, cognitive abilities, muscle mass and function, body composition, bone mineral density, skin and hair condition, pubic hair, urogenital atrophy, vaginal dryness, dry eyes, health in autoimmune conditions, vasomotor instability, breast tenderness, symptoms of premenstrual syndrome, and a combination thereof.

DETAILED DESCRIPTION

A. Definitions

Figure 1:
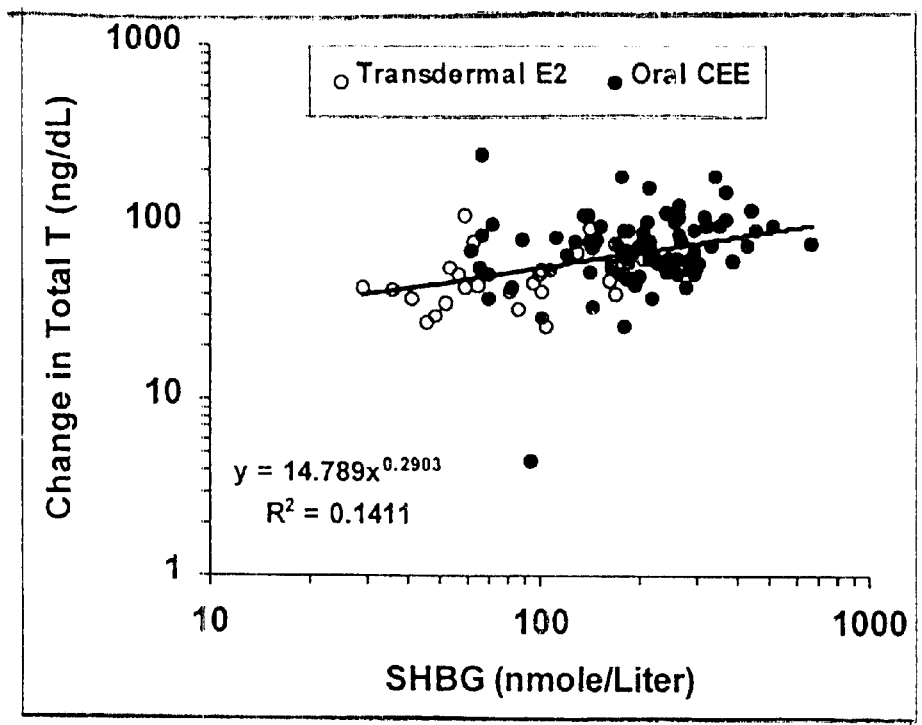
FIG. 1 shows the change in total testosterone level versus baseline SHBG level during application of transdermal testosterone patch (300 mcg/day nominal delivery) to patients concomitantly receiving transdermal estradiol or oral conjugated equine estrogens.

In describing and claiming the present invention, the following terminology will be used.

The singular forms "a," "an," and "the" include plural referents unless the context clearly dictates otherwise. Thus, for example, reference to "a transdermal patch" includes reference to one or more of such transdermal patches, and reference to "an estrogen" includes reference to one or more of such estrogens.

"Sex hormone" refers to any hormone which affects the growth or function of the reproductive organs, or the development of secondary sex characteristics. In one aspect, sex hormones include, but are not limited to androgens, estrogens, progestins, and other hormones which are known in the art.

"Androgenic steroid," or "androgen," refer to a steroid, natural or synthetic, which exerts its biological or pharmacological action primarily by binding to androgen receptors. Examples include, but are not limited to: testosterone, methyltestosterone, androstenedione, adrenosterone, dehydroepiandrosterone, oxymetholone, fluoxymesterone, methandrostenolone, testolactone, pregnenolone, 17α-methylnortestosterone, norethandrolone, dihydrotestosterone, danazol, androsterone, nandrolone, stanozolol, ethylestrenol, oxandrolone, bolasterone, mesterolone, testosterone propionate, testosterone cypionate, testosterone phenylacetate, and testosterone enanthate, testosterone acetate, testosterone buciclate, testosterone heptanoate, testosterone decanoate, testosterone caprate, testosterone isocaprate, as well as esters, derivatives, prodrugs, and isomers thereof.

"Testosterone" refers to the compound having the IUPAC names (17β)-17-Hydroxyandrost-4-en-3-one, and $\Delta^4$-androsten-17β-ol-3-one, as well as their isomers. Testosterone is listed in the Merck Index, entry no. 9322, at page 1569, 12th ed., (1996).

"Estrogen", and "estrogenic hormone" refer to any substance, natural or synthetic, that exerts a biological or pharmacological action primarily by binding to estrogen receptors. Examples include but are not limited to: 17-β-estradiol, 17-α-estradiol, estriol, estrone, and phytoestrogens. These estrogens may be derivatized or modified to form, for example, conjugated equine estrogens, esterified estrogens, ethinyl estradiol, etc. Examples of esterified estrogens include but are not limited to: estradiol-3,17-diacetate, estradiol-3-acetate, estradiol-17-acetate, estradiol-3,17-divalerate, estradiol-3-valerate, estradiol-17-valerate. Also included are selective estrogen receptor modulators (SERMS), for example raloxifene, available under the tradename Evista® from Eli Lilly, and the like. The estrogens may also be present as salts, (e.g., as sodium estrogen sulfate), isomers, or prodrugs.

Also included, are phytoestrogens which are plant-derived estrogens. Isoflavones are one major form of phytoestrogen and have a common diphenolic structure that resembles the structure of potent synthetic estrogens such as diethylstilbesterol and hexestrol. Major isoflavones found in humans include, but are not limited to genistein, diadzein, and equol.

"Oral estrogens" refers to any estrogen which is in a dosage form suitable for oral administration. Conjugated equine estrogens, esterified estrogens and micronized estradiol are examples of oral estrogens. Commercially available oral estrogen products include conjugated equine estrogens available under the trade name Premarin® from Wyeth-Ayerst Laboratories, esterified estrogens available under the trade name Estratab® from Solvay Pharmaceuticals, and micronized 17-β estradiol available under the trade name Estrace® from Bristol Meyers Squibb.

"Progestin," or "progestogen" refer to any substance, natural or synthetic, that exerts a biological or pharmacological action primarily by binding to progestin receptors. Examples include, but are not limited to: progesterone, medroxy-progesterone acetate, norethindrone, and norethindrone acetate, esters, derivatives, prodrugs, and isomers thereof. Progestin has been administered to women in order to achieve a variety of effects. Examples without limitation include providing endometrial safety during concomitant estrogen administration, and providing effective contraception. While the amount of progestin required to achieve such effects may vary from woman to woman, methods for determining appropriate or effective amounts of progestin in order to achieve a designed purpose or effect, are well known to those of ordinary skill in the art.

"Sex hormone binding globulin", or "SHBG", also known as sex hormone binding protein (SHBP) and testosterone estradiol binding globulin (TeBG), refers to a serum protein that binds a variety of sex hormones with high affinity (See Table 1; from Dunn et al., *Transport of Steroid Hormones: Binding of 21 Endogenous Steroids to Both Testosterone-Binding Globulin and Corticosteroid-Binding Globulin in Human Plasma, J. Clinical Endocrinology and Metabolism,* Vol. 53:58–67 (1981)). Represented binding affinity constants (K values) for particular sex hormones and SHBG are provided in Table 1 as follows. (adapted from Dunn et al. 1981)

TABLE 1

| Sex Hormone | K ($10^5$ Liter/mole) |
| --- | --- |
| androstanediol | 1300 |
| androstenediol | 1500 |
| androstenedione | 29 |
| androsterone | 14 |
| dehydroepiandrosterone | 66 |
| dihydrotestosterone | 5500 |
| estradiol | 680 |
| estriol | 4.3 |
| estrone | 150 |
| progesterone | 8.8 |
| 17-hydroxyprogesterone | 9.9 |
| testosterone | 1600 |

For the purposes of this application, SHBG binding affinity constants exceeding about $1 \times 10^6$ Liter/mole indicate high affinity binding.

The structure and proposed functions of SHBG have been described and characterized. See, for example, Rosner et al., *Sex Hormone-Binding Globulin Mediates Steroid Hormone Signal Transduction at the Plasma Membrane, J. Steroid Biochem. Mol. Biol.* Vol. 69:481–5 (1999); Petra, P. H. *The plasma Sex Steroid Binding Protein (SBP or SHBG). A Critical Review of Recent Developments on the Structure, Molecular Biology, and Function, J. Steroid Biochem. Mol. Biol.,* Vol. 40:735–53 (1991). A variety of methods have been used to quantify the serum concentrations of SHBG, including ammonium sulfate precipitation, gel filtration, equilibrium dialysis, dextran-coated charcoal, and radioimmunoassay. See, for example, Khan et al., *Radioimmunoassay for Human Testosterone-Estradiol-Binding Globulin, J. Clinical Endocrinology and Metabolism,* Vol. 54:705–710 (1982). Using a validated monoclonal immuno-radiometric assay (Endocrine Sciences, Calabassas Hills, Calif.), the mean serum SHBG level in healthy premenopausal women was found to be 84 nmole/Liter and the normal range 36 to 185 nmole/Liter. Serum SHBG levels are known to be elevated in women treated with oral estrogens, estrogen-containing oral contraceptives, clomiphene, tamoxifen, raloxifene, phenytoin, and sodium valproate, as well as in women who are pregnant, hyperthyroid, have chronic liver disease and HIV-infection. See for example, Bond et al., *Sex Hormone Binding Globulin in Clinical Perspective, Acta. Obstet. Gynecol. Scand.,* Vol. 66:255–262 (1987); Miller et al. *Transdermal Testosterone Administration in Women with Acquired Immunodeficiency Syndrome Wasting: A Pilot Study, J. of Clinical Endocrinology and Metabolism,* Vol. 83:27172725 (1998).

"Administration," and "administering" refer to the manner in which a drug is presented to a subject. Administration can be accomplished by various routes well-known in the art such as oral, and non-oral methods.

"Oral administration" can be achieved by swallowing, chewing, or sucking of an oral dosage form comprising the drug. "Non-oral administration" represents any method of administration in which a drug composition is not provided in a solid or liquid oral dosage form, wherein such solid or liquid oral dosage form is traditionally intended to substantially release and/or deliver the drug in the gastrointestinal tract beyond the mouth and/or buccal cavity. Such solid dosage forms include conventional tablets, capsules, caplets, etc., which do not substantially release the drug in the mouth or in the oral cavity.

It is appreciated that many oral liquid dosage forms such as solutions, suspensions, emulsions, etc., and some oral solid dosage forms may release some of the drug in the mouth or in the oral cavity during the swallowing of these formulations. However, due to their very short transit time through the mouth, or oral cavity, the release of drug from these formulations in the mouth, or oral cavity, is considered de minimus or insubstantial. Thus, buccal patches, adhesive films, sublingual tablets, and lozenges that are designed to release the drug in the mouth are non-oral compositions for the present purposes.

Thus, the term "non-oral" includes parenteral, topical, inhalation, implant, occular, nasal, and vaginal or rectal formulations and administrations. Further, implant formulations are to be included in the term "non-oral," regardless of the physical location of implantation.

"Parenteral" administration can be achieved by injecting a drug composition intravenously, intra-arterially, intramuscularly, intrathecally, or subcutaneously, etc.

"Topical formulation" means a composition in which the drug may be placed for direct application to a skin surface and from which an effective amount of drug is released. Examples of topical formulations include but are not limited to ointments, creams, gels, transdermal patches, sprays, vaginal rings, and pastes. "Transdermal" refers to the route of administration that facilitates transfer of a drug through a skin surface wherein a transdermal composition is administered to the skin surface.

Transdermal administration can be accomplished by applying, pasting, rolling, attaching, pouring, pressing, rubbing, etc., of a transdermal preparation onto a skin surface. These and additional methods of administration are well-known in the art.

"Transdermal delivery system," "transdermal patches" or simply "patches" refer to a matrix or liquid reservoir type of delivery device which is used to transdermally deliver defined doses of a substance, over a specific application period.

One example of a transdermal patch for administering an androgenic steroid in accordance with this invention is a matrix-type patch which comprises an occlusive backing that is impermeable to the androgen steroids and defines the face or top surface of the patch and a solid or semisolid matrix layer comprised of a homogeneous blend of the hormone, a polymeric pressure sensitive adhesive carrier, and optionally one or more skin permeation enhancers. Matrix patches are known in the art of transdermal drug delivery. Examples without limitation, of adhesive matrix transdermal patches are those described or referred to in U.S. Pat. Nos. 5,122,383 and 5,460,820 which are incorporated by reference in their entirety.

Another example of a transdermal patch for administering an androgenic steroid in accordance with this invention is a liquid reservoir system (LRS) type patch which comprises androgen, and other optional ingredients, such as a permeation enhancer, in a carrier vehicle. The carrier vehicle comprises a fluid of desired viscosity, such as a gel or ointment, which is formulated for confinement in a reservoir having an impermeable backing and a skin contacting permeable membrane, or membrane adhesive laminate providing diffusional contact between the reservoir contents and the skin. For application, a peelable release liner is removed and the patch is attached to the skin surface. LRS patches are known in the art of transdermal drug delivery. Examples without limitation, of LRS transdermal patches are those described or referred to in U.S. Pat. Nos. 4,849,224, 4,983, 395, which are incorporated by reference in their entirety.

"Skin," "skin surface," "derma," "epidermis," and similar terms are used interchangeably herein, and refer to not only the outer skin of a subject comprising the epidermis, but also to mucosal surfaces to which a drug composition may be administered. Examples of mucosal surfaces include the mucosal of the respiratory (including nasal and pulmonary), oral (mouth and buccal), vaginal, introital, labial, and rectal surfaces. Hence the terms "transdermal" encompasses "transmucosal" as well.

"Coadministration" and similar terms refer to administration of multiple substances to one individual, either simultaneously or sequentially. Thus, with reference to estrogen and androgen, the term includes any situation in which women are receiving oral estrogen and non-oral androgen. The term does not imply that the estrogen and androgen have to be administered at the same time. Rather, as long as a woman is receiving oral estrogen, administration of non-oral androgen will be within the present definition for "coadministration". It should be understood that the estrogen and the androgen need not be provided in a single product or by an identical route to be "coadministered".

The terms "formulation" and "composition" are used interchangeably herein. The terms "pharmaceutical" and "drug" are also used interchangeably to refer to a pharmacologically active substance or composition. These terms of art are well-known in the pharmaceutical and medicinal arts.

"Total serum level", "total blood level", and "endogenous serum level," refer to the total serum levels of androgen or estrogen, including all protein-bound and free androgen or estrogen. Certain proteins such as albumin bind androgen or estrogen with a low affinity such that these sex hormones are functional (bioavailable) (i.e., produce their known or intended biological effect). By contrast, some proteins such as SHBG bind androgen or estrogen with high affinity to render them non-functional. One of skill in the art knows how to measure and characterize these types of bindings. See, for example Dunn et al.

Thus, the term "total testosterone serum level" refers to the sum of: (1) free testosterone; (2) testosterone which is weakly bound to serum proteins, such as albumin-bound testosterone; and (3) testosterone which is tightly bound bound to high affinity binding serum proteins, such as SHBG-bound testosterone.

The term "protein-bound" includes all types of protein bindings.

Total serum testosterone can be measured by known assay techniques such as a radioimmunoassay (RIA). See for example the RIA procedure used by Endocrine Sciences, Inc. (Calabassas Hills, Calif.). This procedure is based on the published RIA by Furuyama et al., *Radioimmunoassay for Plasma Testosterone, Steroids.* 1970;16:415–428. With this assay method, the normal range of total serum testosterone levels measured in healthy premenopausal women by Endocrine Sciences, Inc. was reported to be 14 to 54.3 ng/dL (Miller et al. 1998).

"Endogenous free testosterone level" or "physiological free testosterone level," shall refer to the free testosterone (FT) serum level that is normally found in adult women without symptoms associated with testosterone deficiency and/or testosterone excess, and/or imbalanced estrogen/androgen symptoms.

"Bioavailable", "serum bioavailable", and similar terms refer to androgen or estrogen that is not bound to SHBG. Therefore androgen which is "free" (unbound) or "weakly bound to" (easily dissociates from) serum albumin is considered to be bioavailable to tissues. Because of the high binding capacity (non-saturability) of albumin for testosterone, the serum concentration of albumin-bound testosterone will, in general, be proportional to the concentration of free testosterone. The proportionality factor corresponds to the product of the albumin-testosterone binding constant ($3.6 \times 10^4$ L/mole) and the serum albumin concentration (expressed in mole/Liter). See, Vermeulen et al., *A Critical Evaluation of Simple Methods for the Estimation of Free Testosterone in Serum, J. of Clinical Endocrinology and Metabolism* Vol. 84:3666–3672 (1999). Since the concentration of serum albumin is maintained within a relatively narrow range (e.g. 4–5 g/dL; $5.8 \times 10^{-4}$–$7.6 \times 10^{-4}$ mole/Liter), this proportionality factor is approximately 22. As a consequence of this relationship the concentration of bioavailable testosterone may be approximately 23 times the concentration of free testosterone, independent of the concentrations of total testosterone and SHBG.

The concentration of bioavailable testosterone is commonly measured using an ammonium sulfate precipitation method. See, for example, Nankin et al. *Daytime Titers of Testosterone, LH, Estrone, Estradiol, and Testosterone-Binding Protein: Acute Effects of LH and LH-Releasing Hormone in Men, J. Clinical Endocrinology Metabolism,* Vol. 41:271–81 (1975). Using this method the normal range of bioavailable testosterone levels measured in healthy premenopausal women by Endocrine Sciences, Inc. was reported to be 1.6 to 12.7 ng/dL, or about 2 to 13 ng/dL.

"Free," "unbound," or similar terms, refers to the androgen or estrogen which is unattached to any protein, such as SHBG, or albumin. Therefore, androgen or estrogen which is not protein bound is considered "free".

By way of example without limitation, terms such as "free testosterone," "unbound testosterone," "serum free testosterone," refer to the testosterone in the serum that is not protein bound. Serum free testosterone levels can measured by a variety of laboratory methods, including equilibrium dialysis, ultrafiltration, an analogue RIA method, and by calculation from the levels of total testosterone, SHBG and albumin. See, for example, Winters et al. *The Analog Free Testosterone Assay: Are the Results in Men Clinically Useful?, Clinical Chemistry* Vol. 44:2178–2182 (1998); see also, Vermeulen et al. (1999). The equilibrium dialysis method, is currently believed to provide the most accurate results. See, Mathor et al., *Free Plasma Testosterone Levels During the Normal Menstrual Cycle, J. Endocrinol Invest* Vol. 8:437–41 (1985). Using this method the normal range of free testosterone levels measured in healthy premenopausal women by Endocrine Sciences, Inc. was reported to be 1.3 to 6.8 pg/mL, or about 2 to 7 pg/mL.

"Woman" refers to a human female who benefits from an androgen or estrogen supplementation in any way. In one aspect, the female may be menopausal due to age, oophorectomy, or ovarian failure. In another aspect, the female may be receiving oral estrogens for beneficial effects such as to prevent or retard bone loss, to prevent or retard changes in blood lipids which might otherwise predispose the woman to cardiovascular disease. In yet another aspect, the female may display a deficiency, or imbalance of estrogen and androgenic hormones. In yet another aspect, the female may be receiving oral estrogens for contraception.

"Improving health" refers to reducing, improving, or preventing the incidence and/or intensity of symptoms associated with androgenic steroid deficiency. Examples of such symptoms include but are not limited to: sexual dysfunction, which can manifest in loss of sexual desire, decreased sensitivity to sexual stimulation, decreased arousability and capacity for orgasm, diminished vital energy, depressed mood, diminished sense of well-being, increased shyness, loss of muscle mass and function, unfavorable body composition, i.e., lean to fat mass ratio, thinning and loss of pubic hair, urogenital atrophy, dry and brittle scalp hair, dry skin, decreased cognitive abilities, dry eyes, autoimmune phenomena, and a combination thereof.

Increases and decreases in the presence and severity of such symptoms may be ascertained through various devices known in the art for evaluating each particular symptom. For example, sexual function in women may be evaluated using self-assessment questionnaires, such as the Brief Index of Sexual Functioning for Women, (Taylor et al 1994); Derogatis Interview for Sexual Functioning, Derogatis, L., *The Derogatis interview for Sexual Functioning (DISF/DISF-SR): an introductory report, J. Sex. Marital Ther.* Winter 23(4):291–304 (1997); and other questionnaires, such as Derogatis et al., *Psychological assessment measures of human sexual functioning in clinical Trials, Int. J. Impot. Res.,* May 10 Suppl. 2:S13–20 (1998); as well as by genital blood flow methods (Laan 1998). Muscle mass, body composition and bone mineral density are commonly measured using dual energy x-ray absorptiometry (DEXA). Mood, well-being and neurocognitive function can be measured by the Beck Depression Inventory (Beck et al 1961), the Psychological General Well-being Index (Dupuy 1984), and a battery of neurocognitive function tests. Dry eye syndrome can be assessed by tear function tests, e.g., osmolality, volume, flow rate, Shirmer's test, by use of artificial tear preparations, and by subjective questionnaires. See, for example, Mathers et al. *Menopause and Tear Function: The Influence of Prolactin and Sex Hormones on Human Tear Production, Cornea* Vol. 17:353–8 (1998). Immune function can be assessed by the titres of circulating auto-antibodies, by the counts of CD4+ and CD8+ lymphocytes, and by the symptomatology of particular autoimmune disorders, e.g. systemic lupus erythematosis, rheumatoid arthritis, etc.

"Elevated", as used in connection with SHBG levels, refers to an SHBG serum concentration measured in a given woman that is greater than the mean value for healthy premenopausal women reported by the clinical laboratory in which the SHBG level is measured. For example, a value obtained by using the immunoradiometric assay methodology of Endocrine Sciences using their immunoradiometric assay would be considered elevated if it is greater than 84 nmole/Liter. A "substantially elevated" SHBG level refers to an SHBG serum concentration in a given woman that is greater than the upper limit of the normal range for healthy premenopausal women reported by the clinical laboratory in which the SHBG level is measured. For example, a value obtained by using the immunoradiometric assay methodology of Endocrine Sciences would be considered substantially elevated if it were greater than 185 nmole/Liter. In view of the different methods used to measure SHBG in different clinical reference laboratories and the corresponding variations in mean values and normal ranges reported by them, the definitions for elevated and substantially elevated SHBG values given above are applicable to any validated method with properly determined normal ranges.

"Effective amount" refers to an amount of a substance which is sufficient to achieve its intended purpose or effect. Various biological factors may affect the ability of a delivered substance to perform its intended task. Therefore, an "effective amount" may be dependent on such biological factors. By way of example without limitation, a woman having an SHBG serum level of 225 nmole/L may require a greater testosterone dosage to achieve an intended effect, than a woman having an SHBG serum level of 100 nmole/L. Therefore, while the testosterone dosages in such women would vary, each dosage would be considered to be an "effective amount" as long as it achieves its desired effect. Determination of an "effective amount" is well within the ordinary skill in the art.

Many evaluations may be employed for measuring the achievement of desired effects in the case of androgen and estrogen delivery, which are well known in the art. Such evaluations may be performed by a physician, or other qualified medical personnel, and may include physical examination, blood tests, etc.

"Therapeutic effect" refers to a desired result which is achieved to some degree. In the context of androgen and estrogen supplementation as presented in the present patent application, a number of desired results are referred to as "improving health." In one aspect, therapeutic effects may be achieved by delivering an "effective amount" of a substance capable of achieving the desired result to a selected degree. While the achievement of therapeutic effects may be measured by a physician or other qualified medical personnel using evaluations known in the art, it is recognized that individual variation and response to treatments may make the achievement of therapeutic effects a subjective decision.

Concentrations, amounts, solubilities, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

For example, a concentration range of 0.5 to 15 pg/ml should be interpreted to include not only the explicitly recited concentration limits of 0.5 pg/ml and 15 pg/ml, but also to include individual concentrations within that range, such as 0.5 pg/ml, 0.7 pg/ml, 1.0 pg/ml, 5.2 pg/ml, 11.6 pg/ml, 14.2 pg/ml, and sub-ranges such as 0.5–2.5 pg/ml, 4.8–7.2 pg/ml, 6–14.9 pg/ml, etc. This interpretation should apply regardless of the breadth of the range or the characteristic being described.

B. The Invention

Recent research has shown that androgens, and particularly testosterone, contribute substantially to a woman's health and well-being. Ebert, et al., U.S. Pat. No. 5,460,820, in one aspect, teaches a composition and method for administering testosterone transdermally via a patch delivery system. These compositions and methods maintain total testosterone serum blood levels in a "physiological range" of between about 15 to 80 ng/dL by means of transdermally administering about 50 to 500 mcg/day of testosterone from a testosterone matrix. It is recognized that non-oral delivery of androgens is safer to the liver and provides more sustained delivery than oral routes since the first pass metabolism effects are bypassed. On the other hand, oral delivery of estrogens allows for an improved serum lipid profile. However, it has been discovered that the above-stated total testosterone serum levels for females may not be an accurate indicator of therapeutically effective testosterone levels in women with elevated, or substantially elevated SHBG levels, such as those women receiving oral estrogens.

The binding of testosterone to SHBG is known to decrease the transport of testosterone to androgen sensitive tissues, e.g. tissues expressing androgen receptors. Such binding is also known to decrease the metabolic clearance rate of testosterone in both men and women. See, for example, Vermeulen et al. *Metabolic Clearance Rate and Interconversion of Androgens and the Influence of the Free Androgen Fraction, J. Clinical Endocrinology and Metabolism* Vol 48:320–326 (1979); Longcope et al. *Free Estradiol, Free Testosterone, and Sex Hormone-Binding Globulin in Perimenopausal Women, J. Clinical Endocrinology and Metabolism* Vo. 64:513–518 (1987). As a consequence of the influence of SHBG levels on testosterone binding and clearance, the serum levels of total, free, and bioavailable androgen that are attained by administering androgen to a given individual will be dependent on the SHBG level of that individual. However, the influence of SHBG levels on the attained serum levels of androgen cannot be precisely predicted from current knowledge and experimental data are needed.

To provide such data, pharmacokinetic studies were performed in three groups of surgically menopausal women who were administered a 300 mcg/day testosterone transdermal matrix patch twice-a-week for 7 days. One group had received no estrogen replacement therapy (ERT) for at least one month, the second group was receiving transdermal estadiol (E2) at a dosage of 0.1 mg/day, and the third group was receiving oral conjugated equine estrogens (CEE) at a dosage of 1.25 mg/day. Measurements of the SHBG level, obtained prior to patch application, and of total and free testosterone levels, obtained before and during the second 3.5 day patch application period, were made by Endocrine Sciences. The resultant hormone data (mean±SEM) for the three groups of surgically menopausal women participating in the clinical study is summarized in Table 2 below.

It should be noted that the normal range for SHBG levels is 36 to 185 nmol/L using the Endocrine Sciences assay. Further, changes in total testosterone and free testosterone levels represent the time-average changes from change from baseline levels during a 3.5 day patch application.

TABLE 2

| Hormone (unit) | No ERT n = 19 | Transdermal E2 (0.1 mg/day) n = 12 | Oral CEE (1.25 mg/day) n = 13 |
|---|---|---|---|
| SHBG (nmol/L) | 85.6 ± 9.6 | 90.8 ± 12.9 | 226.3 ± 13.5 |
| Changes in Total T (ng/dl) | 57.2 ± 4.4 | 53.6 ± 7.2 | 70.8 ± 9.6 |
| Changes in Free T (pg/mL) | 4.60 ± 0.40 | 4.20 ± 0.70 | 2.56 ± 0.30 |

In the above table:
E2 is estradiol
T is testosterone
CEE is conjugated equine estrogens As shown in Table 2, the mean SHBG level in the oral estrogen group was approximately 2.5-fold larger than the other groups and exceeded the upper limit of the normal range. SHBG levels in the transdermal estrogen group were comparable to the women who did not receive estrogen replacement therapy (ERT). The mean increase in total serum testosterone levels during patch application, i.e. the time-averaged change from baseline, was approximately 30% greater in the oral estrogen group in comparison to the other two groups.

In contrast the mean increase in free serum testosterone level in the oral estrogen group was approximately 40% lower than in the other two groups. These findings indicate that by reducing testosterone clearance, elevated SHBG levels lead to an increase in the total serum levels of testosterone obtained during transdermal testosterone administration. However, despite the elevation in total serum levels, the free serum testosterone levels, and by inference, the bioavailable serum testosterone levels, are reduced by the elevated SHBG levels, presumably due to the increased binding of testosterone by SHBG. These findings are new and unexpected and could not have been predicted from earlier studies.

Figure 2:
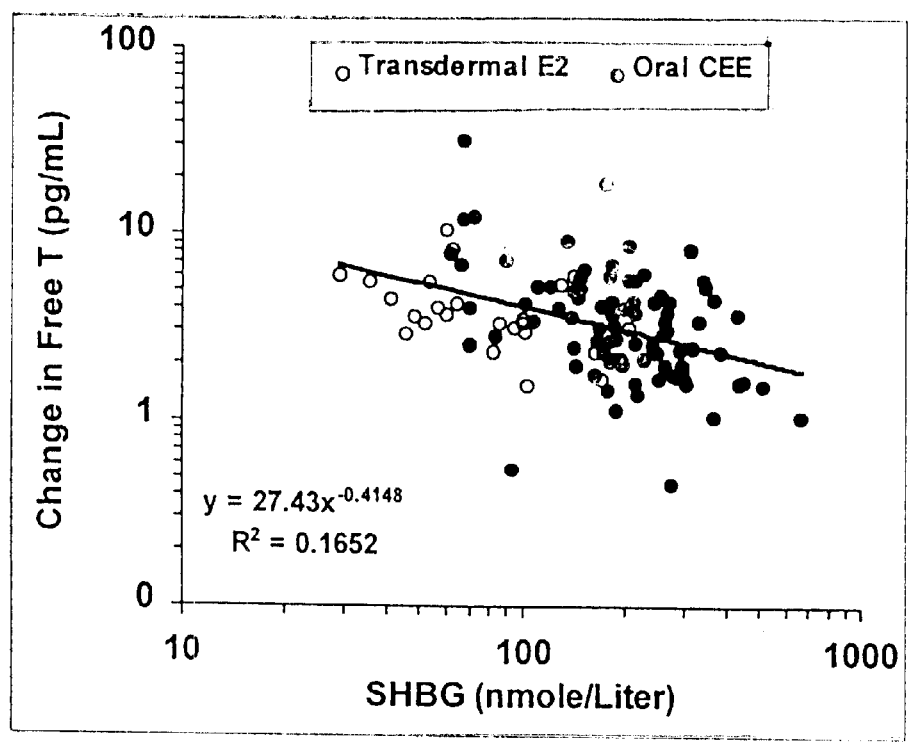
FIG. 2 shows the change in free testosterone level versus baseline SHBG level during application of transdermal testosterone patch (300 mcg/day nominal delivery) to patients concomitantly receiving transdermal estradiol or oral conjugated equine estrogens.

As a further illustration of the novel effects of SHBG on testosterone levels, the individual increments of total serum testosterone and free serum testosterone, obtained during 300 mcg/day transdermal testosterone administration to surgically menopausal women receiving transdermal or oral estrogen, are plotted versus the individual SHBG levels in FIGS. 1 and 2, respectively. As depicted on logarithmic scales, the increments in total serum testosterone become larger with increasing SHBG levels, whereas the increments in free testosterone become smaller as the SHBG levels increase.

To further illustrate the novel and unexpected influence of elevated SHBG levels on the non-oral administration of testosterone, Table 3 below provides estimates of the testosterone delivery rate needed to achieve a given increase in free testosterone (FT) were made as a function of the SHBG level using the power-law regression equation given in FIG. 2. As shown in Table 3, the necessary delivery rate to achieve a given increase (change) in FT increases markedly as the SHBG level increases. For example, the delivery rate needed to achieve an increase of 15 pg/mL in a patient whose SHBG level is 700 nmol/Liter is estimated to be 2484 mcg/day, a value substantially greater than taught in the prior art.

TABLE 3

| | SHBG (nmol/L) | | | | | | |
|---|---|---|---|---|---|---|---|
| Change in FT | 50 | 84 | 100 | 200 | 400 | 600 | 700 |
| (pg/mL) | Estimated Delivery Rate (mcg/day) | | | | | | |
| 1 | 55 | 69 | 74 | 98 | 131 | 155 | 166 |
| 2.5 | 139 | 172 | 185 | 246 | 328 | 388 | 414 |
| 5 | 277 | 344 | 369 | 492 | 656 | 777 | 828 |
| 10 | 554 | 687 | 739 | 985 | 1313 | 1553 | 1656 |
| 15 | 831 | 1031 | 1108 | 1477 | 1969 | 2330 | 2484 |

For the delivery rates given above, the changes in total testosterone level (ng/dL) corresponding to a desired change in free testosterone level and a given SHBG level can be predicted using the power-law regression equation shown in FIG. 1. Table 4 below provides an illustration of such predictions. As shown in Table 4, the changes in total testosterone level corresponding to a given change in free testosterone level increase markedly as the SHBG level increases. For example, the case corresponding to a change in free testosterone of 15 pg/mL in a patient whose SHBG level is 700 nmole/Liter (i.e. a delivery rate of 2484 mcg/day), the predicted increase in total testosterone is 820 ng/dL.

TABLE 4

| | SHBG (nmol/L) | | | | | | |
|---|---|---|---|---|---|---|---|
| Change in FT | 50 | 84 | 100 | 200 | 400 | 600 | 700 |
| (pg/mL) | Predicted Changes in Total Testosterone (ng/dL) | | | | | | |
| 1 | 9 | 12 | 14 | 23 | 37 | 49 | 55 |
| 2.5 | 21 | 31 | 35 | 57 | 92 | 123 | 137 |
| 5 | 43 | 61 | 69 | 113 | 184 | 245 | 273 |
| 10 | 85 | 123 | 139 | 226 | 368 | 490 | 547 |
| 15 | 128 | 184 | 208 | 339 | 553 | 736 | 820 |

It should be appreciated that in extrapolating the findings and predictions of Tables 2, 3 and 4 to an actual patient, one must add the patient's baseline testosterone level (i.e. the level of total or free testosterone prior to treatment) to the expected change in testosterone level from the treatment. For individuals with baseline levels that are subnormal, the final hormone levels attained by treatment will be close to the change itself.

The above findings and predictions indicate that androgen administration to women on oral estrogens, or who have elevated SHBG levels in general, would produce free and/or bioavailable testosterone levels that would be significantly lower compared to women who are on non-oral estrogen therapy or who have low or normal SHBG levels. In addition, women on oral estrogen therapy, or women with elevated SHBG levels in general, would require androgen doses that may exceed those previously considered optimal in women with normal SHBG levels. Further, the administration of such doses would produce levels of total serum testosterone above the generally recognized normal ranges. It should also be noted that for some therapeutic applications, e.g. short term applications of androgens, the desired therapeutic levels of free and/or bioavailable testosterone could also be greater than the corresponding normal physiological ranges. Accordingly, the present invention provides methods, compositions, and kits for administering an androgenic steroid to improve the health of a woman, under conditions where the woman's SHBG levels are elevated.

C. The Various Aspects

In one aspect, the invention presents a method and a kit for administering sex hormones, such as androgens and estrogens to women. In another aspect, the present invention presents a method and kit for non-orally administering androgenic steroids to a woman having elevated SHBG levels, in order to alleviate symptoms attributable to an androgenic hormone deficiency. In yet another aspect, the present invention provides a method and kit for non-orally administering androgenic steroids to a woman who is receiving oral estrogen supplementation. In a further aspect, the present invention provides a method and kit for coadministering an orally administered estrogen, and a non-orally administered androgenic steroid. These methods and kits for administering estrogen and/or androgenic steroids have been found useful in improving health, sexual function, and well-being.

In one aspect of the present invention, androgen may be administered at a dose sufficient to achieve a therapeutic effect equivalent to a free testosterone serum level of from about 0.5 to about 30 pg/ml. In another aspect of the invention, androgen may be administered at a dose sufficient to achieve a therapeutic effect equivalent to a free testosterone serum levels of from about 1 to about 15 pg/ml. In another aspect of the invention, androgen may be administered at a dose sufficient to achieve a therapeutic effect equivalent to a free testosterone serum level of from about 1.3 to about 6.8 pg/ml, or from about 2 to about 7 pg/ml. In yet another aspect of the invention, androgen may be administered at a dose sufficient to achieve a therapeutic effect equivalent to a free testosterone serum level of from about 3 to about 10 pg/ml.

In one aspect of the present invention, an androgen may be administered at a dosage sufficient to achieve a therapeutic effect equivalent to a bioavailable testosterone serum level of from about 1 to about 70 ng/dl. In another aspect of the present invention, an androgen may be administered at a dosage sufficient to achieve a therapeutic effect equivalent to a bioavailable testosterone serum level of from about 2 to about 35 ng/dl. In yet another aspect of the present invention, an androgen may be administered at a dosage sufficient to achieve a therapeutic effect equivalent to a bioavailable testosterone serum level of from about 2 to about 13 ng/dl.

In one aspect of the present invention, an androgen may be administered at a dosage sufficient to achieve a therapeutic effect equivalent to a total testosterone serum level of from about 15 to about 1000 ng/dl. In another aspect of the invention an androgen may be administered at a dosage sufficient to achieve a therapeutic effect equivalent to a total testosterone serum level of from about 85 to about 1000 ng/dl. In a further aspect of the invention, the androgen may be administered at a dosage sufficient to achieve a therapeutic effect equivalent to a total testosterone serum level of from about 100 to about 1000 ng/dl.

In one aspect of the invention, an androgen may be administered in a dosage sufficient to achieve a therapeutic effect equivalent to equivalent to a testosterone dosage of at least about 50 mcg/day. In another aspect, an androgen may be administered in a dosage sufficient to achieve a therapeutic effect equivalent to a testosterone dosage of from about 75 to about 3000 mcg/day. In a further aspect, an androgen may be administered at a dosage sufficient to achieve a therapeutic effect equivalent to a testosterone dosage of testosterone of from about 600 to about 3000 mcg/day. In yet another aspect, an androgen may be administered at a dosage sufficient to achieve a therapeutic effect equivalent to a testosterone dosage of testosterone of from about 700 mcg/day to about 3000 mcg/day.

One of the non-oral routes of delivery for an androgen dose is topical administration. Topical formulations may include a skin permeation enhancer(s) to enhance the level of skin flux of the androgen. Examples, without limitation, of skin permeation enhancers that may be used are described or referred to in U.S. Pat. Nos. 5,122,383 and 5,153,997 the disclosures of which as they relate to skin permeation enhancers are incorporated by reference. Further, an index of permeation enhancers is disclosed by David W. Osborne and Jill J. Henke, in their internet publication entitled *Skin Penetration Enhancers Cited in the Technical Literature*, which may be found at the worldwide web address known as: pharmtech.com/technical/osborne/osborne.htm, which is incorporated by reference herein. An effective amount of an enhancer may be incorporated into a pharmaceutically acceptable carrier. Various carriers will be suitable based on the type of delivery formulation desired. By way of example without limitation, when an adhesive matrix transdermal patch is desired, the carrier may be an adhesive. In another aspect, when a liquid reservoir system (LRS) patch is desired, the carrier may be a gel, cream, ointment, lotion, or other suitable formulation known in the art.

Transdermal patches for transdermal delivery of androgenic steroids may be manufactured by conventional techniques used in the art of transdermal drug delivery devices. For instance, androgens, carrier, and enhancers may be mixed in desired proportions to form a homogeneous mixture and incorporated into a transdermal device. Various techniques are known in the art for making various types of transdermal devices such as adhesive matrix patches and liquid reservoir system (LRS) patches.

In addition to transdermal testosterone patches, other non-oral systems for delivering androgens include but are not limited to: intra-muscular injections of testosterone esters, subcutaneous implants of fused testosterone, and topical preparations of testosterone, methyltestosterone and other androgens. Devices and methods for those non-oral applications are well known in the art.

The need for supplementing sex hormones such as estrogen and androgenic steroids should be determined by a physician or other health care professional based on monitoring signs and symptoms of sex hormone deficiency or based on need for pharmacological intervention of conditions that are responsive to hormonal therapy. Not every female will exhibit the same symptoms and it is possible that sex hormone levels might even be within accepted physiological ranges but, based on other factors, for example, increased SHBG, sex hormone supplementation may still be appropriate.

Symptoms of subfunctional levels of androgens, including testosterone, might include, but not be limited to: sexual dysfunction, which can manifest in loss of sexual desire, decreased sensitivity to sexual stimulation, decreased arousability and capacity for orgasm; diminished vital energy; depressed mood; diminished sense of well-being; increased shyness; loss of muscle mass and function; unfavorable body composition, i.e., lean to fat mass ratio; thinning and loss of pubic hair; urogenital atrophy; dry and brittle scalp hair; dry skin; decreased cognitive abilities; dry eyes; autoimmune phenomena or exacerbation thereof, and a combination thereof.

Women who are receiving oral estrogens can also benefit from androgen therapy as it may reduce the breast tenderness that can occur with estrogen usage. Owing to known breast tissue anti-proliferative effects, androgens may also reduce the excess risk of breast cancer associated with estrogen use. It is therefore highly desirable, if not imperative, that testosterone supplementation for a female patient be based on a diagnosis by a physician who prescribes the mode of application, dosage and duration of treatment.

In so far as it is coadministered with androgenic steroids, estrogen, such as conjugated equine estrogen, may be administered orally in a dosage range of between about 0.2 to 3.0 mg/day. The dose may be adjusted according to an individual woman's needs and the potency of estrogen administered. The dose of oral estrogens can be taken in a single daily dose or in two or more smaller quantities. Ideally, for women who are experiencing vasomotor symptoms, the lowest effective dose of estrogen is used to control for vasomotor instability. Lower doses may be used in women who do not suffer vasomotor symptoms but will benefit from other health benefits, such as cardiovascular and bone benefits. In the case of oral contraceptive use, ethinyl estradiol is typically given cyclically in a 21 day on, 7 day placebo regimen.

In one aspect the present invention provides a method and kit for administering a progestin with androgen and estrogen. Progestins are known for administration to women to protect against endometrial hyperplasia. Progestins are also essential active ingredients of many oral contraceptive formulations. In accordance with one aspect of the present invention, progestins may be administered by any method known in the art according to individual need. The amount of progestin which is effective in achieving a desired purpose may vary from woman to woman. Methods for determining an effective amount of progestin, i.e. an amount sufficient to achieve a desired therapeutic effect, are well known to those ordinarily skilled in the art.

Based on the above dosages and laboratory tests, one skilled in the art can readily determine what amount of a particular androgenic steroid or testosterone derivative to administer to achieve the desired androgenic steroid serum levels, which can be achieved using more than one androgenic steroid, or form of testosterone. What is important is that the dose of the androgenic steroid or testosterone derivative be sufficient to benefit the recipient woman without administering too great a dosage. Administering appropriate dosage levels to obtain the optimal risk/benefit ratio is well within the ordinary skill.

In the embodiments contained in the following examples, a dosage of about 50–3000 mcg/day of an androgenic steroid is administered to a woman receiving oral estrogen in an estrogen replacement therapy (ERT) regimen or as an oral contraceptive. Doses in this range are usually sufficient to obtain a therapeutic response. However, the dosage most appropriate for a particular woman can be determined empirically (e.g., by varying the delivery dosage and assessing the resulting effects on libido, sexual function, mood, a general sense of well being, etc.). Therefore, due to the natural variation in hormone sensitivity, the exact dosage is not as critical as is obtaining a resultant physiological response for a particular patient, which can correspond to a total testosterone serum level of from about 15 to about 400 ng/dl, or a free testosterone serum level of from about 0.5 to about 15 pg/mL.

The following examples are intended to be merely illustrative of the various aspects of the invention disclosed herein and are not intended in any way to limit the scope of the claimed invention. Other aspects of the invention that are considered equivalent by those skilled in the art are also within the scope of this invention.

EXAMPLE 1

In surgically menopausal women between the ages of 20 and 55 years, oral estrogen and transdermal testosterone were administered as follows. The estrogen consisted of conjugated equine estrogen (Premarin® tablets) at a daily dose of 0.625 to 2.5 mg. The transdermal testosterone was administered by a matrix type transdermal patch that was applied to the abdomen twice weekly and has a delivery rate of 300 mcg/day. The duration of coadministration was 12 weeks. After 12 weeks, this regimen improved sexual function, mood and well-being in comparison to administration of conjugated equine estrogen alone.

Serum hormone levels measured on this regimen by Endrocrine Sciences (Calabassas Hills, Calif.) were found to be in the following ranges: total testosterone (15.5 to 254.3 ng/dL), free testosterone (1.7 to 33.7 pg/mL), bioavailable testosterone (2.3 to 71 ng/dl), estradiol (5 to 280 pg/mL), and estrone (8 to 410 pg/mL). Levels of sex hormone binding globulin ranged from 62.7 to 563 nmol/L with 92% being elevated and 48% being substantially elevated according to the definitions of "elevated," and "substantially elevated," provided herein. It is noteworthy that 73% of the women on the regimen of oral estrogen and transdermal testosterone achieved total testosterone levels in excess of 80 ng/dL, the upper limit of the normal range generally recognized in the art. In contrast, 78% had a free testosterone level below 6.8 pg/mL (the upper limit of the normal range for Endocrine Sciences), and 97% had a free testosterone level below 15 pg/mL, which is within the therapeutically acceptable range contemplated herein. Similarly, 68% of the women had a bioavailable tesosterone level below 12.7 ng/dL (the upper limit of the normal range for Endocrine Sciences), and 97% had a bioavailable testosterone level below 35 ng/dL, which is within the therapeutically acceptable range contemplated herein.

EXAMPLE 2

A combination of an androgenic compound and an estrogenic compound may be administered to women who are naturally menopausal according the following regimen:

Androgen: topical administration of testosterone in an appropriate carrier vehicle, such as a cream or ointment, that optionally contains a permeation enhancer as needed in order to achieve desired testosterone serum levels. The androgen cream may contain cetyl esters, cetyl alcohol, white wax, glyceryl monosterate, propylene glycol monosterate, methyl stearate, benzyl alcohol, sodium lauryl sulfate, glycerin, and mineral oil. Each gram of the cream contains about 400 mcg testosterone. About 1 gram of the cream is applied to the skin or abdomen at bedtime. Serum concentrations of free testosterone achieved may be in the range of 0.5–15 pg/mL, and total testosterone achieved may be in the range of 30–250 ng/dL.

In order to control the amount of testosterone administered, a meter dosing device may be employed. Dose adjustments can be made on the basis of either symptom relief, e.g. restored libido, or to achieve the desired free testosterone serum concentrations. Ranges for symptomatic relief may vary between 1–20 pg/mL of free serum testosterone.

Estrogenic compound: oral conjugated equine estrogens tablets may be given at a starting dose of 0.625 mg/day. When necessary, doses are adjusted upward to 1.25 mg/day for better control of symptoms, or downward to 0.3 mg/day as vasomotor symptoms subside to maintain bone and serum lipid benefits.

In women who have an intact uterus, it is important that a sufficient amount of progesterone be present in the serum to avoid endometrial hyperplasia that can result from unopposed estrogen replacement therapy.

Benefits of a combined hormone regimen may be perceived by the patient within the first 6 weeks of administration, but variable responses may occur. Typically, hormones are administered on a chronic basis for health maintenance.

EXAMPLE 3

An androgenic compound and an estrogenic compound may be administered to women who are post-menopausal to alleviate signs and symptoms associated with frailty, such as the loss of bone and muscle mass and function, reduced cognitive abilities and diminished energy.

Androgen: intramuscular injection of 150 mg testosterone enanthate on a monthly basis. Testosterone enanthate may be formulated to contain 200 mg per mL in sesame oil. In order to provide 150 mg of testosterone enanthate, the injected dose is 0.75 mL.

Estrogen: oral estrogens are given in a range of 0.3 to 3.0 mg/day.

Administration is performed as long as benefits of treatment are desired and deemed appropriate by a prescribing physician.

EXAMPLE 4

An androgenic compound and an estrogenic compound may be administered to women with premature ovarian failure, e.g., women whose ovarian function permanently ceases prior to age 40.

Androgen: methyltestosterone may be delivered via the buccal route at a dose of 1 mg/day to achieve an improvement in sexual function that is equally efficacious to an improvement produced by testosterone at serum levels of about 50 to 300 ng/dL. The buccal tablet may be a bilayer tablet consisting of a drug layer and a bio-adhesive layer (both 50 mg each). The composition of the drug layer (in weight percent) may be 2% methyltestosterone, 0.75% magnesium stearate, 0.1% FD&C yellow #6, 24% Klucel HXF, and 73.15% mannitol. The composition of the bio-adhesive layer (in weight percent) may be 69.25% polyethylene oxide, 30% carbomer 934P, and 0.75% magnesium stearate. The adhesive side of the tablet is affixed to the gingiva of the upper jaw and the drug side of the tablet faces the overlying buccal mucosa. Drug is absorbed transmucosally as the tablet dissolves over time. The tablet may be applied once daily after breakfast.

Estrogen: Estrace®, Bristol-Myers Squibb Co., an oral micronized estradiol product in tablet form, may be administered at a dosage of 2 mg/day to alleviate menopausal symptoms and prevent bone loss.

In addition a progestin, such as medroxyprogesterone acetate, may be orally administered at a dose of 5 mg/day for the last ten days of each month to induce endometrial sloughing.

While the examples have been directed primarily to the delivery of an androgenic steroid to provide needed supplementation based on determination of a need for such, the administration will be concurrent with the oral administration of estrogen formulations.

What is claimed is:

1. A method of improving health in a woman having an elevated or substantially elevated level of sex hormone binding globulin (SHBG) comprising non-orally administering to said woman an androgenic steroid in an amount sufficient to provide a therapeutic effect in the presence of elevated or substantially elevated SHBG levels.

2. The method of claim 1, wherein the woman is receiving oral estrogen supplementation.

3. The method of claim 2, wherein the oral estrogen and the non-oral androgenic steroid are coadministered.

4. The method of claim 2, wherein said androgenic steroid is a member selected from the group consisting of: testosterone, methyltestosterone, androstenedione, adrenosterone, dehydroepiandrosterone, oxymetholone, fluoxymesterone, methandrostenolone, testolactone, pregnenolone, 17α-methylnortestosterone, norethandrolone, dihydrotestosterone, danazol, oxymetholone, androsterone, nandrolone, stanozolol, ethylestrenol, oxandrolone, bolasterone and mesterolone, testosterone propionate, testosterone cypionate, testosterone phenylacetate, testosterone enanthate, testosterone acetate, testosterone buciclate, testosterone heptanoate, testosterone decanoate, testosterone caprate, testosterone isocaprate, and isomers thereof, and a combination thereof.

5. The method of claim 2, wherein said androgenic steroid is a member selected from the group consisting of: testosterone, dihydrotestosterone, methyltestosterone, and isomers thereof, and a combination thereof.

6. The method of claim 2, wherein said androgenic steroid is administered in a dosage sufficient to achieve a therapeutic effect equivalent to a total testosterone serum level of from about 15 to about 1000 ng/dl.

7. The method of claim 6, wherein said androgenic steroid dosage is sufficient to achieve a therapeutic effect equivalent to a total testosterone serum level of from about 85 to about 1000 ng/dl.

8. The method of claim 6, wherein said androgenic steroid dosage is sufficient to achieve a therapeutic effect equivalent to a total testosterone serum level of from about 100 to about 1000 ng/dl.

9. The method of claim 2, wherein said androgenic steroid is administered in a dosage sufficient to achieve a therapeutic effect equivalent to a free testosterone serum level of from about 0.5 to about 30 pg/ml.

10. The method of claim 9, wherein said androgenic steroid dosage is sufficient to achieve a therapeutic effect equivalent to a free testosterone serum level of from about 1 to about 15 pg/mL.

11. The method of claim 9, wherein said androgenic steroid dosage is sufficient to achieve a therapeutic effect equivalent to a free testosterone serum level of from about 3 to about 10 pg/ml.

12. The method of claim 9, wherein said androgenic steroid dosage is sufficient to achieve a therapeutic effect equivalent to a free testosterone serum level of about 1 to about 7 pg/ml.

13. The method of claim 2, wherein said androgenic steroid is administered in a dosage sufficient to achieve a therapeutic effect equivalent to a bioavailable testosterone serum level of from about 1 to about 70 ng/dl.

14. The method of claim 13, wherein said androgenic steroid dosage is sufficient to achieve a therapeutic effect equivalent to a bioavailable testosterone serum level of from about 2 to about 35 ng/dl.

15. The method of claim 13, wherein said androgenic steroid dosage is sufficient to achieve a therapeutic effect equivalent to a bioavailable testosterone serum level of from about 2 to about 13 ng/dl.

16. The method of claim 2, wherein said androgenic steroid is administered in a dosage sufficient to achieve a therapeutic effect equivalent to a testosterone dosage of at least about 50 mcg/day.

17. The method of claim 16, wherein said androgenic steroid is administered in a dosage sufficient to achieve a therapeutic effect equivalent to a testosterone dosage of from about 75 to about 3000 mcg/day.

18. The method of claim 16, wherein said androgenic steroid is administered in a dosage sufficient to achieve a therapeutic effect equivalent to a testosterone dosage of from about 500 to about 2500 mcg/day.

19. The method of claim 16, wherein said androgenic steroid is administered in a dosage sufficient to achieve a therapeutic effect equivalent to a testosterone dosage of from about 550 to about 2000 mcg/day.

20. The method of claim 2, wherein said non-oral administration is topical administration, or parenteral administration, or a combination thereof.

21. The method of claim 20, wherein said parenteral administration is intramuscular injection, or subcutaneous implantation, or a combination thereof.

22. The method of claim 20, wherein said topical administration is transdermal, transmucosal, or sublingual, or a combination thereof.

23. The method of claim 2, wherein said improved health is manifest by restoration, enhancement, or improvement of a characteristic selected from the group consisting of: sexual desire, stimulation to sexual organs, ability to achieve orgasm, pleasure in sexual activity, frequency of sexual activity, vital energy, sense of well-being, mood and sense of emotional well being, shyness, cognitive abilities, muscle mass and function, body composition, bone mineral density, skin and hair condition, pubic hair, urogenital atrophy, vaginal dryness, dry eyes, health in autoimmune conditions, vasomotor instability, breast tenderness, symptoms of premenstrual syndrome, and a combination thereof.

24. The method of claim 2, wherein said estrogen is administered in a dosage sufficient to achieve a therapeutic effect equivalent to a conjugated equine estrogen dosage of from about 0.2 to about 3.0 mg/day.

25. The method of claim 2, wherein said orally administered estrogen is a member selected from the group consisting of: 17β-estradiol, 17α-estradiol, conjugated equine estrogen, esterified estrogen, micronized estradiol, sodium estrogen sulfate, ethinyl estradiol, estrone, tibolone, selective estrogen receptor modulator (SERM), phytoestrogen, and isomers thereof, and a combination thereof.

26. The method of claim 2, wherein said orally administered estrogen is a conjugated equine estrogen.

27. The method of claim 2, wherein said orally administered estrogen is an esterified estrogen.

28. The method of claim 2, wherein said orally administered estrogen is micronized estradiol.

29. The method of claim 2, further comprising administering an effective amount of a progestin sufficient to provide endometrial safety.

30. The method of claim 2, further comprising administering an amount of progestin sufficient to provide effective contraception.

* * * * *